United States Patent
Watterson, III et al.

(10) Patent No.: US 6,448,305 B1
(45) Date of Patent: Sep. 10, 2002

(54) ANTIMICROBIAL ACRYLIC MATERIAL

(75) Inventors: Robert S. Watterson, III; William D. Hanrahan, both of Charlotte, NC (US)

(73) Assignee: Microban Products Company, Huntersville, NC (US)

( * ) Notice: Subject to any disclaimer, the term of this patent is extended or adjusted under 35 U.S.C. 154(b) by 0 days.

(21) Appl. No.: 09/530,469

(22) PCT Filed: Sep. 8, 1999

(86) PCT No.: PCT/US99/20531

§ 371 (c)(1),
(2), (4) Date: Jun. 9, 2000

(87) PCT Pub. No.: WO00/14128

PCT Pub. Date: Mar. 16, 2000

Related U.S. Application Data

(60) Provisional application No. 60/099,391, filed on Sep. 8, 1998.

(51) Int. Cl.[7] .................................................. A61K 6/00
(52) U.S. Cl. ....................................................... 523/122
(58) Field of Search ......................................... 523/122

(56) References Cited

U.S. PATENT DOCUMENTS 5,587,407 A * 12/1996 Terry et al. .................. 523/122

* cited by examiner

*Primary Examiner*—Edward J. Cain
(74) *Attorney, Agent, or Firm*—Dougherty, Clements &Hofer

(57) ABSTRACT

An acrylic material having antimicrobial characteristics that inhibit bacterial growth includes an acrylic polymer and an antimicrobial agent incorporated therein. The acrylic polymer is a conventional acrylonitrile compound. The antimicrobial agent is incorporated into the amorphous zones of the molecular structure of the acrylic polymer. When the acrylic material is formed using conventional techniques, the antimicrobial additive is incorporated into the amorphous zones of the molecular structure of the acrylic polymer using a solubilizing agent carrier, thereby incorporating the antimicrobial agent into the acrylic polymer. The antimicrobial additive in the acrylic material, incorporated in the manner above, results in substantive controlled migration from within the acrylic material to the surface of the acrylic material, until a point of equilibrium is reached.

20 Claims, No Drawings

ANTIMICROBIAL ACRYLIC MATERIAL

This application claims the benefit of provisional application No. 60/099,391 filed on Sep. 8, 1998.

FIELD OF THE INVENTION

This invention relates generally to antimicrobial acrylic materials, and more particularly to acrylic materials having antimicrobial compounds or chemicals incorporated into an acrylic polymer.

BACKGROUND OF THE INVENTION

Acrylic is widely used in numerous consumer products to provide a durable product having desirable product appearance, colorability and chemical resistance. The ability to produce generally transparent or translucent characteristics in acrylic makes acrylic an ideal material for many different applications and, particularly, to enhance the appearance of a product. Manufacturers use acrylic to produce products having good color finish while also providing the qualities of substantial abrasion-resistance and chemical resistance.

For example, acrylic materials are incorporated into bathtubs, showers, whirlpools, bathroom and kitchen flooring and paneling used in homes, hotels, hospitals, restaurants and other residential or commercial environments. The acrylic can be applied or formed to have varying thicknesses depending on a desired manipulability and the expected wear from abrasion or continuous exposure to water and reactive chemicals. In another example, acrylic is incorporated into panels used in automobiles and recreation vehicles. The acrylic may be molded or laminated with the panels to provide a vehicle having a high quality surface appearance and colorability. In another example, acrylic fibers are used in the textile industry to provide resilient or stretchable yarns and fabric having good colorability and durability which are in turn incorporated into clothing.

However, these acrylic based products are under constant exposure to bacteria, fungi and microbes that exist in their respective environments. For example, acrylic based flooring or paneling as well as acrylic based coatings used on flooring are particularly susceptible to bacterial and microbial development. People and moveable objects, which are carriers of bacteria and microbes, heavily traffic the floorings. This results in a continual deposit of such bacteria and microbes on the floorings and consequently develops a "bio-burden" or a continuous resource for contamination. Additionally, bathrooms and kitchens, whether incorporated in domestic settings or commercial settings, are environments where contaminated parts of the body or contaminated utensils are washed. Unfortunately, residual contamination typically remains on the flooring or paneling to repopulate. In another example, clothing containing acrylic based yarns or fibers provide harbors for odor-causing bacteria and fungi transferred from a wearer's body.

Each of these environments are a constant source of bacterial, fungal or microbial contamination. Not only are these acrylic based products contaminated by the bacteria, fungi and microbes in these environments, but these environments also aid in the proliferation of the bacteria, fungi and microbes. The presence of humidity or moisture in these environments is generally conducive to the growth of bacteria, fungi and microbes. These bacteria, fungi and microbes can grow and multiply on the surfaces of the acrylic based products, and significant levels of contamination can build over time.

To counter the presence and growth of microbes on the surface of acrylic based products, a disinfectant is typically applied to the surface, such as by washing, spraying or wiping. Unfortunately, the applied disinfectant provides only temporary removal of the microbes on the surface because, as previously mentioned, the associated environment is a resource that rebuilds a bio-burden and provides further contamination. Reapplication of the disinfectant is costly, time consuming, non-durable and only temporarily counters the presence and growth of microbes.

Further, non-thorough cleaning of the acrylic based products leaves residual contamination as previously mentioned. Without attention to detail when cleaning the acrylic based products, residual contamination is more likely to exist. Additionally, by applying the disinfectant or other biocide to the surface of the acrylic based product, a residual of the disinfectant or biocide enters the environment and may negatively impact the environment.

What is needed is an antimicrobial agent that can be incorporated, or incorporated, into an acrylic material at the time of manufacture and that survives incorporation. In particular, what is needed is an antimicrobial agent incorporated into an acrylic material that is free from toxic effect and is durable over the lifespan of the acrylic material. Further needed is an acrylic material having an antimicrobial agent incorporated into an acrylic polymer which will migrate to the surface of the acrylic material as needed to provide appropriate protection. Further needed is an acrylic material having antimicrobial compounds or chemicals incorporated in the material and formed by extruding, sheet thermoforming, calendaring, casting, coating, brushing, spraying, pouring or other conventional acrylic forming techniques, that exhibits controlled migration of the antimicrobial compounds or chemicals through the material. Further needed is an acrylic material having antimicrobial compounds or chemicals incorporated in the polymeric material that exhibits substantially the same physical characteristics as an acrylic polymeric material that does not have antimicrobial compounds or chemicals incorporated therein.

SUMMARY OF THE INVENTION

The present invention is an acrylic material having antimicrobial characteristics that inhibits bacterial, fungal, microbial and other pathogen or non-pathogen growth. Antimicrobial agents, compounds or chemicals are incorporated into the acrylic material during manufacture. The term "incorporate" as used herein in relation to antimicrobial agents or additives, is defined to mean residing in the interstitial spaces of the polymeric matrix of the polymeric material.

The antimicrobial agent is incorporated into the amorphous zones of the acrylic polymer at the time of manufacture of an acrylic based product and survives incorporation. The incorporated antimicrobial agent is free from toxic effect and is durable over the lifespan of the acrylic material. The antimicrobial agent that is incorporated into the acrylic polymer migrates to the surface of the acrylic material as needed to provide appropriate protection. The acrylic material, that exhibits controlled migration of the antimicrobial compounds or chemicals through the material, may be processed by extruding, sheet thermoforming, calendaring, casting, coating, brushing, spraying, pouring or other conventional acrylic forming techniques. The acrylic material exhibits substantially the same physical characteristics as an acrylic material that does not have antimicrobial compounds or chemicals incorporated therein.

The acrylic material include acrylonitriles, such as polyacrylonitrile (PAN), polymethacrylonitrile (PMAN) and acrylonitrile-methylmethacrylate (P[AN-MMA]), polyacrylic acid (PAA), polymethacrylic acid (PMAA), polymethylacrylate (PMA), polyethylacrylate (PEA), polybutylacrylate (PBA) and polymethylmethacrylate (PMMA).

In one embodiment of the present invention, the acrylic material, having antimicrobial compounds or chemicals incorporated in the same and that exhibits controlled migration of the antimicrobial compounds to the surface of the material, is formed into a sheet by calendaring or sheet thermoforming. In another embodiment of the present invention, the acrylic material, having antimicrobial compounds incorporated in the same and that exhibits controlled migration of the antimicrobial compounds to the surface of the material, is formed into fibers, such as textile fibers by extrusion or spinning processing techniques. In another embodiment of the present invention, the acrylic material having antimicrobial compounds or chemicals incorporated in the same and that exhibits controlled migration of the antimicrobial compounds to the surface of the material, is poured into a cast form and an acrylic product is derived from the cast form. In another embodiment of the present invention, the acrylic material, having antimicrobial compounds or chemicals incorporated in the same and that exhibits controlled migration of the antimicrobial compounds to the surface of the material, is applied to flooring, such as by coating, pouring, spraying or brushing.

When forming an acrylic product by extrusion techniques, a solubilizing agent carrier system, such as a surfactant, is used to incorporate the antimicrobial additive into the amorphous zones of the molecular structure of the acrylic. When preparing acrylic based fibers, cast forms or floorings, the antimicrobial additive does not require the solubilizing agent carrier system to incorporate the antimicrobial additive into the amorphous zones of the molecular structure of the acrylic. The levels of antimicrobial additive in the acrylic material, incorporated in the manner above, result in a substantive controlled migration from the amorphous zones of the molecular structure of the acrylic to the surface of the acrylic material, until a point of equilibrium is reached. As the surface of the acrylic material is abraded during use and this equilibrium is disrupted, additional migration is stimulated, until equilibrium is again reached. Products formed with the acrylic material include, without limitation, sinks, wash basins, automotive panels, architectural panels, fitness products, swimming pools, seamless flooring, outdoor signs, skylights, whirlpools, modular tubs, indoor and outdoor spas, boat decks, boat hulls, boat interiors, automobile panels, textile fibers and coatings.

The acrylic material is formed by selecting an antimicrobial agent to correspond to the acrylic, determining whether a solubilizing agent carrier system is required, combining any required solubilizing agent carrier system with the selected antimicrobial agent, incorporating the antimicrobial agent into an acrylic batch, and forming a desired acrylic based product

OBJECTS OF THE INVENTION

The principal object of the invention is to provide an acrylic material having antimicrobial protection incorporated in the acrylic material.

Another, more particular object of the invention is to provide an acrylic material having antimicrobial protection incorporated in the acrylic material in a cost-effective, non-toxic and durable way.

Another object of the invention is to provide an acrylic material having antimicrobial compounds or chemicals incorporated in the acrylic material that is formable into a sheet, a fiber or a cast and that exhibits a controlled migration of the antimicrobial compounds or chemicals throughout the acrylic polymer.

Another object of the invention is to provide an acrylic material having antimicrobial compounds or chemicals incorporated in the acrylic material that has physical, mechanical and surface appearance characteristics similar to acrylic materials that do not have antimicrobial compounds or chemicals incorporated in the acrylic material.

Another, more particular, object of the invention isto provide an acrylic material having antimicrobial compounds or chemicals incorporated in the acrylic material that has a chemical resistance, tensile strength and water absorption resistance similar to acrylic materials that do not have antimicrobial compounds or chemicals incorporated in the acrylic material.

Another object of the invention is to provide a product formed from an acrylic material having an antimicrobial agent which is insoluble in water, thereby preventing any leaching of the agent during use of the product.

Another object of the invention is to provide an acrylic material in which an antimicrobial agent can migrate on demand from within the material to the surface of the material if some of the agent is removed from the surface of the acrylic material by abrasion.

Another, more particular, object of the invention is to provide an acrylic material having an antimicrobial compound incorporated in the acrylic material that does not exhibit sublimation of the antimicrobial compound at ambient temperatures.

DETAILED DESCRIPTION OF THE INVENTION

In the most basic form of the present invention, an acrylic material is made having an acrylic polymer and a broad spectrum antimicrobial agent that are together processed and formed into a product including, but not limited to a sheet, a fiber and a cast form. The acrylic material may be applied to the cast form and flooring using conventional techniques such as by coating, spraying, pouring and brushing. The broad spectrum antimicrobial agent associated therewith inhibits bacterial, fungal, viral and other pathogen or non-pathogen growth.

Preferably, a predetermined concentration of antimicrobial agent is incorporated into the acrylic polymer from which an acrylic product is made. The term "incorporate" as used herein in relation to antimicrobial agents or additives, is defined to mean residing in the interstitial spaces of the polymeric matrix of the polymeric material. Thus, an effective amount of an antimicrobial agent or additive (e.g., 5-chloro-2-(2,4-dichlorophenoxy)phenol) is incorporated therein. Concentrations of active ingredients or antimicrobial agents range from about 0.1% to about 3% by weight of the acrylic material. The antimicrobial agent incorporated into the acrylic polymer surprisingly exhibits controlled migration through the acrylic polymer.

Acrylic may be prepared by various methods including bulk, solution, emulsion, suspension and granulation polymerization. This polymer may also be obtained in liquid monomer or filly polymerized beads, sheets, panels or rods. After the acrylic polymer is prepared, the acrylic polymer may be processed by casting, pouring, sheet thermoforming, extrusion, calendaring, coating, brushing, spraying and machining with conventional tools to form a desired end product.

The acrylic polymer is selected from conventional acrylics including acrylonitiles, such as polyacrylonitrile (PAN), polymethacrylonitrile (PMAN) and acrylonitrile-methylmethacrylate (P[AN-MMA]), polyacrylic acid (PAA), polymethacrylic acid (MAA), polymetylacrylate (PMA), polyethylacrylate (PEA), polybutylacrylate PBA) and polymethylmethacrylate (PMMA). Homopolymer PAN is a polar crystallizing polymer and may be processed into fiber by spinning from solution PMAN generally does not appear to crystallize and is characterized by transparency and creep resistance. P[AN-MMA] is commonly used to produce substantially thick, transparent end products that require high impact strength, chemical resistance and weathering resistance. PMMA is characterized by having excellent transparency, good rigidity, acceptable impact and abrasion resistance, outstanding weatherability and good general chemical resistance. Additionally, PMMA may be clear or colorable and transparent or translucent.

Acrylic based sheets may be used for various end products including seamless flooring outdoor signs, skylights, whirlpools, modular tubs, indoor and outdoor spas, boat surfaces and automobile panels. The acrylic based end products are preferably prepared by sheet thermoforming, sheet extrusion or calendaring. Sheet thermoforming includes straight vacuum thermoforming, air pressure thermoforming, freeforming and draping techniques to deform the sheet into a desired final product. Emulsions of acrylic, such as latex, may be used as a coating or paint for walls, ceilings, flooring or automotive panels. Acrylic based fibers may be used in articles of clothing such as shirts, sweaters, gloves, pants and other clothes. Acrylic based fibers may be prepared by extruding fibers or monofilaments from powder or pellet form polymer feed. Additionally, acrylic based fibers may be prepared by extrusion or spinning acrylic from solution.

The antimicrobial agent, which is non-toxic and free of heavy metal, is selected from conventional antimicrobial substances such as halogenated phenyl ethers, halogenated salicylanilides, sesquiterpene alcohols, halogenated carbanilides, bisphenolic compounds, general phenols, formaldehyde, quaternary ammonium compounds, pyridine derivatives, zinc based compounds and hexachlorophane. The antimicrobial agent is preferably a chlorinated phenol and, more preferably, 5-chloro-2-(2,4-dichloro-phenoxy) phenol such as manufactured under the tradename of Triclosan or Irgasan by Ciba-Geigy. An alternative antimicrobial agent is polyhexamethylene biguanide hydrochloride (PHMB). Other chemical compounds having known antimicrobial characteristics may also be used in the present invention.

The antimicrobial agent incorporated into the acrylic polymer is characterized by the agent moving from areas of high concentrations of agent to low concentrations of agent. In a preferred embodiment of the present invention, the antimicrobial agent chosen is substantially insoluble in water which minimizes or eliminates any leaching of the agent when the acrylic material is exposed to water. By controlling the amount of antimicrobial agent incorporated into the acrylic polymer, migration of antimicrobial agent from within the acrylic material to the surface of the acrylic material is accomplished and optimid while maintaining the physical and mechanical properties of the acrylic material. Surprisingly, the acrylic material having the antimicrobial agent incorporated therein has no substantial diminishment in physical and mechanical properties such as chemical and abrasion resistance, tensile strength, impact strength and water absorption resistance, nor is there substantial diminishment in the appearance of the acrylic material.

Incorporating an appropriate amount of antimicrobial agent into the acrylic polymer is important. High concentrations of antimicrobial agent incorporated into the acrylic polymer can result in a degradation of the physical properties of the acrylic material. Additionally, high concentrations of antimicrobial agent increases production costs because of the added expense associated with using more antimicrobial agent. Low concentrations of antimicrobial agent incorporated into the acrylic polymer minimize the effective migration of antimicrobial agent to the surface of the acrylic material. An appropriate concentration range of antimicrobial agent in the acrylic material is necessary to effectively provide the acrylic material with nontoxic, antimicrobial protection and without sacrificing desirable physical properties of the acrylic polymer and incurring unnecessary production costs.

The antimicrobial agent is incorporated into an acrylic polymer master batch prior to forming the acrylic material. When forming acrylic based products using extrusion techniques, the antimicrobial agent is preferably combined in a pre-determined amount, corresponding to a desired efficacy of the acrylic material, with a solubilizing agent carrier system, for example a surfactant, that is compatible with the antimicrobial agent and introduced to the acrylic polymer master batch. For example, 5-chloro-2-(2,4-dichlorophenoxy)phenol was combined with the solubilizing agent carrier system and incorporated into the amorphous zones of the acrylic polymer during manufacture of the acrylic material. After the antimicrobial agent is incorporated into the acrylic polymer to produce the acrylic material, the acrylic material is applied to flooring by coating, spraying, brushing, pouring or other conventional flooring application techniques.

Fiber reinforcements, such as glass fibers, may be incorporated in the acrylic material to provide structural and physical reinforcement to the acrylic material. The fiber reinforcements are selected from high modulus fibers such as glass fibers, carbon fibers, metal fibers and aromatic polyamide fibers. The glass fibers may be chopped fibers ranging from about 5 mm to about 50 mm in length or may be continuous fibers in woven or non-woven forms.

The acrylic material having the antimicrobial agent incorporated therein is further resistant to the growth of fungus, yeast, virus, and gram positive and gram negative bacteria including *S. aureus, E. coli, K. pneumoniae,* and Salmonella. Organic antimicrobial agents have limited incorporability into polymer compositions because organic antimicrobial agents typically have a vaporization point less than the temperatures involved during formation of the polymer compositions. For example, 5-chloro-2-(2,4-dichlorophenoxy)phenol has a melting range of about 135° F. to about 165° F. and a vaporization point of about 400° F., whereas the temperatures generally associated with forming plastics are typically above 400° F. In that respect, if the antimicrobial agent is introduced into the polymer during manufacture, the agent typically vaporizes and does not become incorporated into the polymer. Alternatively, the antimicrobial agent may cross-link with the polymer. Cross-linking of the antimicrobial agent with the polymer is undesirable because the physical properties of the polymer can be degraded. Furthermore, cross-linking prevents the migration of antimicrobial agent through the acrylic material.

In the manufacture of the acrylic material described herein, the acrylic polymer may be prepared at ambient temperature to minimize or eliminate vaporization of the antimicrobial agent. Furthermore, as previously described hereinabove, the antimicrobial agent survives incorporation into the acrylic polymer and exhibits controlled migration through the acrylic material despite the highly crystalline structure of the acrylic polymer, particularly when the acrylic polymer is PAN.

In one embodiment of the present invention, the antimicrobial agent is incorporated in the acrylic material by first incorporating the agent into the solubilizing agent carrier system, as previously described, prior to its addition to the acrylic resin master batch. The solubilizing agent carrier system containing the antimicrobial agent is combined with the acrylic polymer in liquid form using conventional batch processing techniques. In that respect, the antimicrobial agent is added as a component to the acrylic polymer in a let-down ratio which results in a final concentration of active ingredient of from about 0.1 percent to about 3.0 percent by weight of the acrylic material. When acrylic based fibers are desired, the antimicrobial agent is added as a component to the acrylic polymer in a let-down ratio which results in a final concentration of active ingredient of about 0.5 percent by weight of the acrylic based fiber. When acrylic based flooring is desired, the antimicrobial agent is added as a component to the acrylic polymer in a let-down ratio which results in a final concentration of active ingredient of about 0.25 percent by weight of the acrylic based flooring. When acrylic based cast form is desired, the antimicrobial agent is added as a component to the acrylic polymer in a let-down ratio which results in a final concentration of active ingredient from about 0.25 percent to about 0.5 percent by weight of the acrylic based cast form.

Different types of products formed from the acrylic material include bathtubs, sinks, wash basins, automotive panels, architectural panels, boats, fitness products, swimming pools and other home amenities.

In use, the antimicrobial agent migrates through the acrylic material to the exposed surface of the acrylic material from the amorphous zones of the acrylic polymer until equilibrium of the internal vapor pressure is reached. If the antimicrobial substance on the surface of the acrylic material is removed by friction, or other abrading means, the antimicrobial agent moves to the surface until the agent's internal vapor pressure is once again at equilibrium.

The incorporation of the antimicrobial agent in the acrylic polymer in a sheet form or cast form results in a surprisingly improved abrasion resistance in comparison with acrylic materials without an incorporated antimicrobial agent. The acrylic material having the antimicrobial agent incorporated therein does not exhibit sublimation of the antimicrobial agent at ambient temperatures.

SUMMARY OF THE ACHIEVEMENT OF THE OBJECTS OF THE INVENTION

It is readily apparent that we have invented an acrylic material having antimicrobial protection incorporated in an acrylic end product. The present invention provides an acrylic material having antimicrobial protection incorporated in the acrylic material in a cost-effective, non-toxic and durable way. The present invention provides an acrylic material having antimicrobial compounds or chemicals incorporated in the acrylic material that is formable into a sheet, a fiber, a coating or a casting and that exhibits a controlled migration of the antimicrobial compounds or chemicals throughout the acrylic polymer. The present invention provides an acrylic material having antimicrobial compounds or chemicals incorporated in the acrylic material that has physical, mechanical and surface appearance characteristics similar to acrylic materials that do not have antimicrobial compounds or chemicals incorporated in the acrylic material. The present invention provides an acrylic material having antimicrobial compounds or chemicals incorporated in the acrylic material that has a chemical and abrasion resistance, tensile strength and water absorption resistance similar to acrylic materials that do not have antimicrobial compounds or chemicals incorporated in the acrylic material. The present invention provides a product forced from an acrylic material having an antimicrobial agent which is insoluble in water, thereby preventing any leaching of the agent during use of the product. The present invention provides an acrylic material in which an antimicrobial agent can migrate on demand from within the material to the surface of the material if some of the agent is removed from the surface of the acrylic material by abrasion. The present invention provide an acrylic material having an antimicrobial compound incorporated in the acrylic material that does not exhibit sublimation of the antimicrobial compound at ambient temperatures.

It is to be understood that the foregoing description and specific embodiments are merely illustrative of the best mode of the invention and the principles thereof, and that various modifications and additions may be made to the apparatus by those skilled in the art, without departing from the spirit and scope of this invention, which is therefore understood to be limited only by the scope of the appended claims.

What is claimed is:

1. An acrylic material having antimicrobial characteristics comprising:
    an acrylic polymer;
    an antimicrobial agent incorporated into said acrylic polymer; and
    said antimicrobial agent being selected from the group consisting of 5-chloro-2-(2,4-dichlorophenoxy)phenol and polyhexamethylene biguanide hydrochloride;
    wherein said antimicrobial agent exhibits controlled migration through said acrylic polymer to the surface of the acrylic material.

2. An acrylic material according to claim 1 wherein said antimicrobial agent exhibits controlled migration through said acrylic polymer when an imbalance of vapor pressure of the antimicrobial agent demands equalization.

3. An acrylic material according to claim 1 wherein said antimicrobial agent is present in the composite in an amount of from about 0.1 percent to about 3.0 percent by weight.

4. An acrylic material according to claim 1 further comprising a solubilizing agent carrier system for incorporating said antimicrobial agent with said acrylic polymer.

5. An acrylic material according to claim 1 wherein said acrylic polymer is selected from the group consisting of acrylonitriles, polyacrylonitrile (PAN), polymethacrylonitrile (PMAN), acrylonitrile-methylmethacrylate (P[AN-MMA]), polyacrylic acid (PAA), polymethacrylic acid (PMAA), polymethylacrylate (PMA), polyethylacrylate (PEA), polybutylacrylate (PBA) and polymethylmethacrylate (PMMA).

6. An acrylic material for extruding or spinning into fibers for use in textiles having antimicrobial characteristics comprising:
    an acrylic polymer;
    an antimicrobial agent incorporated into said acrylic polymer; and
    said antimicrobial agent being selected from the group consisting of 5-chloro-2-(2,4-dichlorophenoxy)phenol and polyhexamethylene biguanide hydrochloride;

wherein the antimicrobial agent exhibits controlled migration through said acrylic polymer and to the surface of the acrylic material.

7. An acrylic material according to claim 6 wherein said antimicrobial agent is present in the material in an amount of from about 0.1 percent to about 3.0 percent by weight.

8. An acrylic material according to claim 6 wherein said antimicrobial agent exhibits controlled migration through said acrylic polymer when an imbalance of vapor pressure of the antimicrobial agent demands equalization.

9. An acrylic material according to claim 6 wherein said acrylic polymer is selected from the group consisting of acrylonitriles, polyacrylonitrile (PAN), polymethacrylonitrile (PMAN) and acrylonitrile-methylmethacrylate (P[AN-MMA]).

10. An extruded acrylic material having antimicrobial characteristics comprising:
    an acrylic resin;
    a solubilizing agent carrier;
    an antimicrobial agent incorporated with said acrylic resin; and
    said antimicrobial agent being selected from the group consisting of 5-chloro-2-(2,4-dichlorophenoxy)phenol and polyhexamethylene biguanide hydrochloride;
    wherein said antimicrobial agent exhibits controlled migration through said acrylic resin and to the surface of the acrylic material.

11. An acrylic material according to claim 10 wherein said antimicrobial agent is present in the material in an amount of from about 0.1 percent to about 3.0 percent by weight.

12. An acrylic material according to claim 10 wherein said antimicrobial agent exhibits controlled migration through said acrylic resin when an imbalance of vapor pressure of the antimicrobial agent demands equalization.

13. An acrylic material according to claim 10 wherein said solubilizing agent carrier is a surfactant.

14. An acrylic material according to claim 13 wherein said surfactant is triacetin.

15. An acrylic material according to claim 10 wherein said acrylic resin is selected from the group consisting of acrylonitriles, polyacrylonitrile (PAN), polymethacrylonitrile (PMAN), acrylonitrile-methylmethacrylate (P[AN-MMA]), polyacrylic acid (PAA), polymethacrylic acid (PMAA), polymethylacrylate (PMA), polyethylacrylate (PEA), polybutylacrylate (PBA) and polymethylmethacrylate (PMMA).

16. An extruded acrylic material having antimicrobial characteristics comprising:
    an acrylic resin;
    a solubilizing agent carrier comprising triacetin surfactant; and
    an antimicrobial agent incorporated with said acrylic resin;
    wherein said antimicrobial agent exhibits controlled migration through said acrylic resin and to the surface of the acrylic material.

17. An acrylic material according to claim 16 wherein said antimicrobial agent is present in the material in an amount of from about 0.1 percent to about 3.0 percent by weight.

18. An acrylic material according to claim 16 wherein said antimicrobial agent exhibits controlled migration through said acrylic resin when an imbalance of vapor pressure of the antimicrobial agent demands equalization.

19. An acrylic material according to claim 16 wherein said antimicrobial agent is a chlorinated phenol.

20. An acrylic material according to claim 16 wherein said acrylic resin is selected from the group consisting of acrylonitriles, polyacrylonitrile (PAN), polymethacrylonitrile (PMAN), acrylonitrile-methylmethacrylate (P[AN-MMA]), polyacrylic acid (PAA), polymethacrylic acid (PMAA), polymethylacrylate (PMA), polyethylacrylate (PEA), polybutylacrylate (PBA) and polymethylmethacrylate (PMMA).

* * * * *